United States Patent [19]

Albertson

[11] 4,108,857
[45] Aug. 22, 1978

[54] IMIDAZOLYLMETHYL METHANOBENZAZOCINES

[75] Inventor: Noel F. Albertson, Schodack, N.Y.

[73] Assignee: Sterling Drug Inc., New York, N.Y.

[21] Appl. No.: 772,984

[22] Filed: Feb. 28, 1977

Related U.S. Application Data

[60] Division of Ser. No. 605,272, Aug. 18, 1975, abandoned, which is a continuation-in-part of Ser. No. 133,400, Apr. 12, 1971, abandoned, which is a continuation-in-part of Ser. No. 856,157, Sep. 8, 1969, abandoned, which is a continuation-in-part of Ser. No. 642,224, May 29, 1967, abandoned, which is a continuation-in-part of Ser. No. 405,244, Oct. 20, 1964, Pat. No. 3,382,249.

[51] Int. Cl.² .................................. C07D 221/26
[52] U.S. Cl. ................................. 260/293.54
[58] Field of Search ............... 260/293.54, DIG. 13

[56] References Cited

U.S. PATENT DOCUMENTS 2,924,603   2/1960   Gordon et al. ............... 260/293.54

*Primary Examiner*—Henry R. Jiles
*Assistant Examiner*—Richard A. Schwartz
*Attorney, Agent, or Firm*—Theodore C. Miller; B. Woodrow Wyatt

[57] ABSTRACT

1,2,3,4,5,6-Hexahydro-3-(Y)-6-($R^1$)-11-($R^2$)-2,6-methano-3-benzazocines, wherein Y is cycloalkyl-lower alkyl, lower alkyl-cycloalkyl-lower alkyl, carboxy-lower alkyl, cyano-lower alkyl, carbamyl-lower alkyl, tetrahydrofurylmethyl, 2-(2- or 3-indolyl)ethyl, amino-lower alkyl, butylcarbamyl, pyridinecarbonyl, (1-lower alkyl-imidazol-5-yl)methyl, 2,2-dimethoxyethyl, lower alkenyl, halo-lower alkenyl or cyano-lower alkenyl, $R^1$ is lower alkyl and $R^2$ is hydrogen or lower alkyl, are obtained starting with the corresponding 3-(H) compounds, in some instances via 3-acylated intermediate amides. The products have useful central depressant and psychomotor action, the preferred species wherein Y is cycloalkyl-lower alkyl or lower alkylcycloalkyl-lower alkyl being useful as analgesic agents in humans.

4 Claims, No Drawings

IMIDAZOLYLMETHYL METHANOBENZAZOCINES

CROSS-REFERENCE TO RELATED APPLICATIONS

This application is a division of my copending application Ser. No. 605,272, filed Aug. 18, 1975 and now abandoned, which is in turn a continuation-in-part of my copending application Ser. No. 133,400, filed Apr. 12, 1971 and now abandoned, which is in turn a continuation-in-part of my copending application Ser. No. 856,157, filed Sept. 8, 1969 and now abandoned, which is in turn a continuation-in-part of my copending application Ser. No. 642,224, filed May 29, 1967 and now abandoned, which is in turn a continuation-in-part of my copending application Ser. No. 405,244, filed Oct. 20, 1964, now U.S. Pat. No. 3,382,249.

FIELD OF THE INVENTION

This invention relates to chemical compositions of matter classified as 1,2,3,4,5,6-hexahydro-2,6-methano-3-benzazocines and to intermediates therefor.

SUMMARY OF THE INVENTION

The invention sought to be patented resides in the concept of 1,2,3,4,5,6-hexahydro-6-lower alkyl-2,6-methano-3-benzazocines in which in the 11-position is optionally attached lower alkyl and in which the nitrogen atom thereof bears the monovalent radical Y which is cycloalkyl-lower alkyl, lower alkylcycloalkyl-lower alkyl, carboxy-lower alkyl, cyano-lower alkyl, carbamyl-lower alkyl, tetrahydrofurylmethyl, 2-(2- or 3-indolyl)ethyl, amino-lower alkyl, butylcarbamyl, pyridinecarbonyl, (1-lower alkyl-imidazol-5-yl)methyl, 2,2-dimethoxyethyl, lower alkenyl, halo-lower alkenyl or cyano-lower alkenyl. My new compounds have in the free base form the structural formula

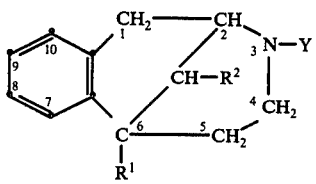

Formula I wherein $R^1$ is lower alkyl and $R^2$ is hydrogen or lower alkyl and Y has the significance indicated hereinabove.

DETAILED DESCRIPTION OF THE INVENTION

As used herein, the term "cycloalkyl" means monovalent radicals derived by removal of one atom of hydrogen from saturated monocyclic hydrocarbons and the term "lower alkylcycloalkyl" means cycloalkyl bearing lower alkyl substituents, the total number of carbon atoms being 4–10. The preferred cycloalkyl and lower alkylcycloalkyl radicals have 3–6 ring carbon atoms, as illustrated by, but not limited to, cyclopropyl, cyclobutyl, 2-methylcyclopropyl, cyclopentyl, 2-ethylcyclopropyl, 1-methylcyclobutyl, cyclohexyl, 3,3-dimethylcyclobutyl, 2-ethylcyclobutyl, 2-propylcyclopropyl, 2-butylcyclohexyl, 2,4-diethylcyclohexyl, and the like.

The term "lower alkyl" used herein means in each instance monovalent radicals of relatively low molecular weight derived from saturated branched and unbranched aliphatic hydrocarbons; the preferred alkyl radicals have 1–4 carbon atoms as illustrated by, but not limited to, methyl, ethyl, n-propyl, isopropyl, and n-butyl.

Thus, when the substituent group Y in Formula I is cycloalkyl-lower alkyl or lower alkylcycloalkyl-lower alkyl it has the structure cycloalkyl-lower alkyleneor lower alkylcycloalkyl-lower alkylenerespectively, wherein cycloalkyl and lower alkyl have the above-indicated significance and the term "lower alkylene" means bivalent radicals derived from saturated aliphatic hydrocarbons of relatively low molecular weight by removal of two hydrogens from one or two carbon atoms thereof; the preferred lower alkylene radicals have 1–4 carbon atoms, as illustrated by, but not limited to, $-CH_2-$, $-CH_2CH_2-$, $-CH_2CH_2CH_2-$, $-CH_2-CH(CH_3)-$, and $CH_2CH_2CH_2CH_2-$. These 1,2,3,4,5,6-hexahydro-3-[(cycloalkyl- or lower alkylcycloalkyl)-lower alkyl]-6-($R^1$)-11-($R^2$)-2,6-methano-3-benzazocines, which have in the free base form the structural formula

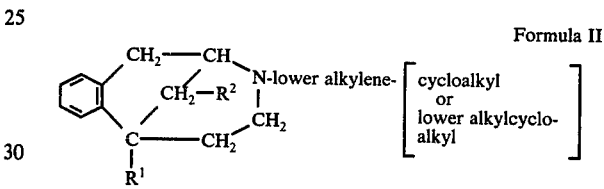

Formula II wherein $R^1$, $R^2$, cycloalkyl, lower alkyl, and alkylene have the same significance indicated hereinabove, are the preferred species of the instant invention. In accordance with the above disclosure it will be appreciated that the N-substituent in these preferred compounds contains a total of 4–14 carbon atoms.

When Y is carboxy-lower alkyl there are included, for example, carboxymethyl, 2-carboxyethyl, 1-carboxyethyl, 3-carboxybutyl, and the like. When Y is cyano-lower alkyl, there are included, for example, cyanomethyl, 2-cyanoethyl, 2-cyanopropyl, 4-cyanobutyl, and the like. When Y is carbamyl-lower alkyl, there are included, for example, carbamylmethyl, 2-carbamylethyl, 4-carbamylbutyl, and the like. When Y is amino-lower alkyl, there are included, for example, 2-aminoethyl, aminoisobutyl, 4-aminobutyl, and the like. When Y is butylcarbamyl, there are included n-butylcarbanyl, isobutylcarbamyl, sec-butylcarbamyl and tert-butylcarbamyl. When Y is pyridinecarbonyl, there are included 2-, 3-, and 4-pyridinecarbonyl. When Y is (1-lower alkylimidazol-5-yl)methyl, there are included (1-methylimidazol-5-yl)methyl, (1-ethylimidazol-5-yl)methyl, (1-isopropylimidazol-5-yl)methyl, (1-n-butylimidazol-5-yl)methyl, and the like. When Y is lower alkenyl, there are included the monovalent lower molecular weight unsaturated aliphatic hydrocarbon radicals containing a double bond, said radicals preferably having 2–6 carbon atoms, for example $CH_2=CH-$, $CH_2=CH-CH_2-$, $CH_2=C(CH_3)-CH_2-$, $CH_3CH=CH-CH_2-$, $CH_2=CH-CH_2CH_2CH_2-$, $(CH_3)_2C=CH-CH_2-$, $CH_3CH_2CH_2-CH=CH-CH_2-$, $CH_3CH_2-CH=CH-CH_2CH_2-$, $CH_2=CH-CH(CH_3)-$, $(CH_3)_2C=CH-CH(CH_3)-$, and the like. When Y is halo-lower alkenyl, there are included the monovalent lower molecular weight unsaturated aliphatic halohydrocarbon radicals containing a double bond and having 1–2 members of the group consisting of chlorine and bromine attached to ethylenic carbon, that is, either one or both of the two ethylenic carbons involved in the —C═C— double-bond bear chlorine or bromine, said radical preferably having 2–5 carbon atoms, for example —CH═CH—Cl, —CH═CH—Br, —CCl═CH$_2$, —CCl═CHCl, —CCl═CHBr, —CH$_2$—CH═C-Cl—CH$_3$, —CH$_2$—CCl═CCl—CH$_3$, —CH═C(Cl)$_2$, —CBr═C(CH$_3$)$_2$, —CH$_2$—CH═CHCl, —CH$_2$C-H$_2$—CH═CCl—CH$_3$, and the like. When Y is cyano-lower alkenyl, there are included the monovalent lower molecular weight unsaturated aliphatic cyanohydrocarbon radicals containing a double bond, and preferably having 3–6 carbon atoms and one or two cyano groups, for example —CH═CH—CN, —C(CN)═CH$_2$, —C(CH$_3$)═CH—CN, —CH$_2$—CH═CH—CN, —CH$_2$CH$_2$—CH═CH—CN, —CH═CH—CH$_2$CH$_2$C-H$_2$—CN, —CH═C(CN)$_2$, and the like.

The new bases (Formula I) of this invention are typically high-boiling liquids which form high-melting, white crystalline hydrochlorides and which have pharmacodynamic activity, in particular, useful central depressant action and psychomotor action. The preferred species of Formula II are particularly useful as anticonvulsants, as antagonists of certain strong analgesic agents such as morphine and meperidine, and especially as analgesic agents.

Generally speaking, my new compounds are obtained by direct or indirect alkylation of the corresponding secondary amines, i.e. the compounds having a hydrogen atom on the nitrogen atom at the 3-position. Thus, in a direct alkylation procedure, 1,2,3,4,5,6-hexahydro-6-(R$^1$)-11-(R$^2$)-2,6-methano-3-benzazocine is heated with an alkylating agent having the formula Y$^1$-An, wherein Y$^1$ is cycloalkyl-lower alkyl, lower alkylcycloalkyl-lower alkyl, cyano-lower alkyl, 2-(2- or 3-indolyl)ethyl, (1-lower alkylimidazol-5-yl)methyl, lower alkenyl, halo-lower alkenyl, or cyano-lower alkenyl, and An is the anion of a strong organic or inorganic acid, for instance a reactive halide or an arylsulfonate, e.g. a tosylate, in the presence of an acid-absorbing medium, for instance an alkali metal carbonate or bicarbonate, e.g. sodium bicarbonate, thereby yielding the desired 1,2,3,4,5,6-hexahydro-3-(Y$^1$)-6-(R$^1$)-11-(R$^2$)-2,6-methano-3-benzazocine. This alkylation reaction is preferably carried out in the presence of a suitable reaction medium such as a lower alkanol, for instance methanol or ethanol, or an N,N-(di-lower alkyl)-lower alkanamide, for instance N,N-dimethylformamide or N,N-dimethylacetamide.

In an indirect procedure, 1,2,3,4,5,6-hexahydro-6-(R$^1$)-11-(R$^2$)-2,6-methano-3-benzazocine is N-acylated by interaction with one molecular equivalent of an acylating agent which is an acid halide or an acid anhydride of an acid having the formula (cycloalkyl or lower alkylcycloalkyl)-lower alkylene-COOH of Y$^2$—COOH in which Y$^2$ is cycloalkyl, tetrahydrofuryl, 2- or 3-indolylmethyl, pyridyl, lower alkenyl, halo-lower alkenyl, or cyano-lower alkenyl, and reducing the resulting amide by treating it with a reducing agent such as lithium aluminum hydride. This reducing agent is effective to reduce the carbonyl of the amide group to —CH$_2$—, without affecting any ethylenic linkages, so that the final product is 1,2,3,4,5,6-hexahydro-3-[(cycloalkyl or lower alkylcycloalkyl)-lower alkyl or Y$^2$]-6-(R$^1$)-11-(R$^2$)-2,6-methano-3-benzazocine, wherein Y$^2$, R$^1$, and R$^2$ have the same meanings indicated hereinabove.

Compounds of Formula I wherein Y is cyano-lower alkyl containing at least two carbon atoms in the lower alkyl moiety are conveniently obtained by N-alkylating 1,2,3,4,5,6-hexahydro-6-(R$^1$)-11-(R$^2$)-2,6-methano-3-benzazocine by treatment with a lower 2-alkenenitrile.

The compounds of Formula I wherein Y is carboxy-lower alkyl are conveniently obtained by hydrolyzing the corresponding compounds wherein Y is cyano-lower alkyl with hot strong mineral acid, for example, concentrated hydrochloric acid.

The compounds of Formula I wherein Y is carbamyl-lower alkyl are conveniently obtained by hydrolyzing the corresponding compounds of Formula I wherein Y is cyano-lower alkyl by treatment with cold strong mineral acid, for example concentrated hydrochloric acid.

The compounds of Formula I wherein Y is amino-lower alkyl and this group is characterized by the aminomethyl moiety, i.e. H$_2$N—CH$_2$—, are conveniently obtained by reducing the corresponding compounds wherein Y is carbamyl-lower alkyl, for example by treatment with lithium aluminum hydride in tetrahydrofuran.

The compounds of Formula I wherein Y is butylcarbamyl are conveniently obtained by interacting 1,2,3,4,5,6-hexahydro-6-(R$^1$)-11-(R$^2$)-2,6-methano-3-benzazocine with the appropriate butyl isocyanate.

The compounds of Formula I wherein Y is 2,2-dimethoxyethyl are conveniently obtained by interacting 1,2,3,4,5,6-hexahydro-6-(R$^1$)-11-(R$^2$)-2,6-methano-3-benzazocine with bromacetaldehyde dimethyl acetal.

My new compounds can exist in stereochemically isomeric forms, that is, optical isomers and geometric isomers. When desired, the isolation or the production of a particular stereochemical form can be accomplished by application of the general principles known in the prior art.

Due to the presence of a basic tertiary amino grouping, the compounds of this invention react with organic and inorganic acids to form acid-addition salts. These acid-addition salts are prepared from any organic acid, inorganic acid (including organic acids having an inorganic group therein), or organo-metallic acid as exemplified by organic mono- and poly-carboxylic acids such as found, for example, in Beilstein's Organische Chemie, 4th Ed., Volumes III, IV, IX, X, XIV, XVII, XIX, XXI, XXII and XXV; organic mono and polysulfonic acid-sulfinic acids such as found, for example in Beilstein Volumes VI, XI, XVI, and XXII; organic phosphonic and phosphinic acids such as found, for example, in Beilstein Volumes XI and XVI; organic acids of arsenic and antimony such as found, for example, in Beilstein Volume XVI; organic heterocyclic carboxylic, sulfonic, and sulfinic acids such as found, for example in Beilstein Volumes XVIII, XXII, and XXV; acidic ion-exchange resins; and inorganic acids of any acid forming element or combination of elements such as found in Mellor, Comprehensive Treatise on Inorganic and Theoretical Chemistry, Longman's, Green and Co., New York, N.Y. Volumes I–XVI. In addition, other salt-forming compounds which are acidic in their chemical properties but which are not generally considered as acids in the same sense as carboxylic or sulfonic acids are also considered to be among the numerous acids which can be used to prepare the acid-addition salt forms of the compounds of this invention. Thus there are also included acidic phenolic compounds such as found, for example, in Volume VI of Beilstein, acidic compounds having "activated" or acidic hydrogen atoms, as for example, picrolonic acid, or barbituric acid derivatives having an acidic proton such as found, for example, in Cox et al. Medicinal Chemistry, Vol. IV, John Wiley and Sons, Inc., New York, N.Y. (1959).

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicyclic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, 2-naphthalenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, arsenic acid, and the like. The acid-addition salts with lactic acid and with ethanesulfonic acid, for example, are water-soluble.

The acid-addition salts are prepared in conventional fashion, for instance either by direct mixing of the acid and the free base form or, when this is not appropriate, by dissolving either or both of the acid and the free base form separately in water or an organic solvent and mixing the two solutions, or by dissolving both the acid and the free base form together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the free base form of my compounds.

The acid-addition salt forms of my new compounds are useful not only as central depressants and psychomotor agents, etc. as hereinabove indicated, but are also useful for characterizing and identifying purposes, and in isolation or purification procedures. Moreover, the acid-addition salts are sources of the free base forms, for instance by reaction with strong bases, and accordingly all of the acid-addition salts, regardless of considerations of solubility, toxicity, physical form, or the like of a particular salt, are useful for the purposes of my invention.

It will be appreciated from the above that if one or more of the characteristics, such as solubility, molecular weight, physical appearance, toxicity, or the like of a given free base or acid-addition salt form of a particular compound render that form less suitable for the purpose at hand, it can be readily converted to another, more suitable form.

By alternative system of nomenclature, the benzazocine compounds of this invention are designated as benzomorphan derivatives, that is, as 2-(Y)-5-($R^1$)-9-($R^2$)-6,7-benzomorphans.

The structures of the compounds of this invention followed from the methods of synthesis which were used and from the elementary analyses of the products obtained.

My invention is illustrated by the following examples without, however, being limited thereto.

EXAMPLE 1

1,2,3,4,5,6-Hexahydro-3-cyclopropylmethyl-6,11-dimethyl-2,6-methano-3-benzazocine A. To a stirred mixture of 8.0 g. of racemic 1,2,3,4,5,6-hexahydro-cis-6,11-dimethyl-2,6-methano-3-benzazocine (which is known also as racemic cis-5,9-dimethyl-6,7-benzomorphan) dissolved in 80 ml. of chloroform and 6 ml. of triethylamine there was added dropwise at room temperature 4.5 g. of cyclopropanecarbonyl chloride. The reaction mixture was stirred for 2 hours and was then washed in a separatory funnel successively with water, dilute hydrochloric acid, and water. The chloroform layer was concentrated under reduced pressure to yield 10.9 g. of racemic 1,2,3,4,5,6-hexahydro-3-cyclopropanecarbonyl-cis-6,11-dimethyl-2,6-methano-3-benzazocine. To a suspension of 4 g. of lithium aluminum hydride in tetrahydrofuran there was added a solution of this product in tetrahydrofuran and the resulting mixture was stirred and refluxed for approximately 5 hours. The reaction mixture was mixed with 8 ml. of water and a few ml. of diethyl ether and the mixture was filtered. The residue was extracted with hot tetrahydrofuran, and this extract and the filtrate were combined and concentrated to yield a residue which weighed 7.4 g. Water and 3 ml. of hydrochloric acid were added to this residue and the mixture was extracted with diethyl ether, the ethereal layer being then discarded. Ammonium hydroxide was added to the aqueous layer and the mixture was extracted with diethyl ether. The ethereal extract was dried and concentrated to yield 6.8 g. of a yellow oil. This oil was distilled under reduced pressure. The fraction distilling at 119°–122° C. at 0.8 mm. pressure weighed 6.0 g. This product was racemic 1,2,3,4,5,6-hexahydro-3-cyclopropylmethyl-cis-6,11-dimethyl-2,6-methano-3-benzazocine having the molecular formula $C_{18}H_{25}N$. A 5 percent (w/v) solution of this base in 95 percent ethyl alcohol was prepared, and when this solution was diluted with four volumes of water a precipitate formed. The base was converted to its hydrochloride. After recrystallization from isopropyl alcohol-diethyl ether, this hydrochloride was obtained as white crystals which weighed 4.5 g. and melted at 249°–251° C. The hydrochloride was soluble in a mixture of 0.42 ml. of N/2 hydrochloric acid and 0.58 ml. of water to the extent of 1 percent, the pH of the 1 percent solution being 1.5; and when the pH of the 1 percent solution was gradually raised by addition of N/10 sodium hydroxide solution, no precipitate formed at pH 7.0.

In an alternative procedure, the above-designated base is obtained by interaction of racemic 1,2,3,4,5,6-hexahydro-cis-6,11-dimethyl-2,6-methano-3-benzazocine with cyclopropylmethyl bromide in the presence of sodium bicarbonate in N,N-dimethylformamide.

B. By interaction of 1,2,3,4,5,6-hexahydro-3-cyclopropylmethyl-cis-6,11-dimethyl-2,6-methano-3-benzazocine hydrochloride, in aqueous solution, with the appropriate sodium salt of each of 1,5-naphthalenedisulfonic acid, pamoic acid [4,4'-methylenebis(3-hydroxy-2-naphthoic acid)], and 3-hydroxy-2-naphthoic acid, and lauryl hydrogen sulfate (containing small amounts of other alkyl hydrogen sulfates), there was obtained the following respective acid-addition salts: 1,5-naphthalenedisulfonate, $(C_{18}H_{25}N)_2.C_{10}H_8O_6S_2$, as white crystals which melted at 306°–309° C. (dec.); hemipamoate, $(C_{18}H_{25}N)_2 \cdot C_{23}H_{16}O_6$) as a light-yellow solid which melted at 140°–205° C.; 3-hydroxy-2-naphthoate, $C_{18}H_{25}N \cdot C_{11}H_8O_3$, as light-yellow crystals which melted at 198°–202° C.; lauryl sulfate (chiefly), $C_{18}H_{25}N \cdot C_{12}H_{26}O_4S$, as white crystals which melted at 79°–95° C.

By interaction of 1,2,3,4,5,6-hexahydro-3-cyclopropylmethyl-cis-6,11-dimethyl-2,6-methano-3-benzazocine free base and 2-naphthalenesulfonic acid there was obtained the 2-naphthalenesulfonic acid addition salt, $C_{18}H_{25}N \cdot C_{10}H_8O_3S$, which melted at 170°–171° C.

C. Resolution of 1,2,3,4,5,6-hexahydro-3-cyclopropylmethyl-cis-6,11-dimethyl-2,6-methano-3-benzazocine into its optical isomers was accomplished using dextro- and levo-dibenzoyltartaric acids. The resolved isomers were converted from the dibenzoyltartrate salt forms into the free base forms and then into the hydrochloride salt forms. The dextro hydrochloride salt form melted at 257°–259° C. and had $[\alpha]_D^{25} +81.6°$ (2% in water) and the levo hydrochloride salt form melted at 258°–260° C. and had $[\alpha]_D^{25} -81.9°$ (2% in water).

EXAMPLE 2

1,2,3,4,5,6-Hexahydro-3-cyclopropylmethyl-6,11-dimethyl-2,6-methano-3-benzazocine Following a procedure similar to that described in Example 1A hereinabove, 6.0 g. of racemic 1,2,3,4,5,6-hexahydro-trans-6,11-dimethyl-2,6-methano-3-benzazocine was N-acylated with 3.3 g. of cyclopropanecarbonyl chloride to yield 7.9 g. of racemic 1,2,3,4,5,6-hexahydro-3-cyclopropanecarbonyl-trans-6,11-dimethyl-2,6-methano-3-benzazocine. This amide (7.9 g.) was reduced for 5 hours with lithium aluminum hydride (3 g.) to yield racemic 1,2,3,4,5,6-hexahydro-3-cyclopropylmethyl-trans-6,11-dimethyl-2,6-methano-3-benzazocine, having the molecular formula $C_{18}H_{25}N$. This base was converted to its hydrobromide, a white crystalline solid which weighed 3.1 g. and melted at 238°–240° C. The solubility of the hydrobromide in water was less than 0.25 percent; and its solubility in 95 percent ethyl alcohol was less than 1 percent (w/v).

EXAMPLE 3

1,2,3,4,5,6-Hexahydro-3-cyclopropylmethyl-6-ethyl-11-methyl-2,6-methano-3-benzazocine Following a procedure similar to that described in Example 1A hereinabove, 9.0 g. of racemic 1,2,3,4,5,6-hexahydro-cis-(6-ethyl-11-methyl)-2,6-methano-3-benzazocine was N-acylated with 4.4 g. of cyclopropanecarbonyl chloride to yield 11.9 g. of racemic 1,2,3,4,5,6-hexahydro-3-cyclopropanecarbonyl-cis-(6-ethyl-11-methyl)-2,6-methano-3-benzazocine as a yellow oil. This amide (11.8 g.) was reduced for four hours with lithium aluminum hydride (2 g.) in tetrahydrofuran to yield 1,2,3,4,5,6-hexahydro-3-cyclopropylmethyl-cis-(6-ethyl-11-methyl)-2,6-methano-3-benzazocine. This base was converted to its hydrochloride, a white crystalline solid which weighed 3.8 g. and melted at 243°–249° C. The solubility of the hydrochloride in water was 20 percent. The pH of a 1 percent solution of the hydrochloride was 5.6; when the pH of this solution was adjusted to 6.5 by addition of N/10 sodium hydroxide solution, a precipitate formed.

EXAMPLE 4

1,2,3,4,5,6-Hexahydro-3-cyclobutylmethyl-6,11-dimethyl-2,6-methano-3-benzazocine Following a procedure similar to that described in Example 1A hereinabove, 3.7 g. of cyclobutanecarbonyl chloride and 5.8 g. of racemic 1,2,3,4,5,6-hexahydro-cis-6,11-dimethyl-2,6-methano-3-benzazocine were interacted to produce 7.4 g. of racemic 1,2,3,4,5,6-hexahydro-3-cyclobutanecarbonyl-cis-6,11-dimethyl-2,6-methano-3-benzazocine as a pale yellow syrup. This amide (7.4 g.) was reduced with lithium aluminum hydride (2.0 g.) in tetrahydrofuran for four hours to yield 5.8 g. of racemic 1,2,3,4,5,6-hexahydro-3-cyclobutylmethyl-cis-6,11-dimethyl-2,6-methano-3-benzazocine, having the molecular formula $C_{19}H_{27}N$, a yellow syrup. This base was converted to its hydrochloride, which weighed 5.3 g. and melted at 270°–271° C. (dec.). The solubility of the hydrochloride in water was less than 0.25 percent; it was soluble in 95 percent ethyl alcohol to the extent of 5 percent (w/v); no precipitate formed when this solution was diluted with four volumes of water; the pH of the thus diluted solution was 6.1.

EXAMPLE 5

1,2,3,4,5,6-Hexahydro-3-(3,3-dimethylcyclobutylmethyl)-6,11-dimethyl-2,6-methano-3-benzazocine Following a procedure similar to that described in Example 1A hereinabove, racemic 1,2,3,4,5,6-hexahydro-cis-6,11-dimethyl-2,6-methano-3-benzazocine was N-acylated with 3,3-dimethylcyclobutanecarbonyl chloride (obtained by interaction of 3,3-dimethylcyclobutanecarboxylic acid with thionyl chloride) to yield 10.7 g. of racemic 1,2,3,4,5,6-hexahydro-3-(3,3-dimethylcyclobutanecarbonyl)-cis-6,11-dimethyl-2,6-methano-3-benzazocine as a viscous yellow syrup. This amide (10.7 g.) was reduced with lithium aluminum hydride (2 g.) in tetrahydrofuran to produce racemic 1,2,3,4,5,6-hexahydro-3-(3,3-dimethylcyclobutylmethyl)-cis-6,11-dimethyl-2,6-methano-3-benzazocine having the molecular formula $C_{21}H_{31}N$. This base was converted to its hydrochloride, a white crystalline solid which weighed 9.3 g. and melted at 240°–241° C. The solubility of this compound in water was 0.5 percent. The pH of the 0.5 percent aqueous solution was 6.8; when the pH was adjusted to 6.8 by addition of N/10 sodium hydroxide solution, a precipitate formed. In 95 percent ethyl alcohol, the solubility of the hydrochloride was 5 percent (w/v); a precipitate formed when this solution was diluted with four volumes of water.

EXAMPLE 6

1,2,3,4,5,6-Hexahydro-3-cyclopentylmethyl-6,11-dimethyl-2,6-methano-3-benzazocine Using a procedure similar to that described in Example 1A hereinabove, 8.0 g. of racemic 1,2,3,4,5,6-hexahydro-cis-6,11-dimethyl-2,6-methano-3-benzazocine was N-acylated with 5.8 g. of cyclopentanecarbonyl chloride to produce 10.7 g. of racemic 1,2,3,4,5,6-hexahydro-3-cyclopentanecarbonyl-cis-6,11-dimethyl-2,6-methano-3-benzazocine. This amide (10.7 g.) was reduced with lithium aluminum hydride (4 g.) in tetrahydrofuran for about 5 hours to produce racemic 1,2,3,4,5,6-hexahydro-3-cyclopentylmethyl-cis-6,11-dimethyl-2,6-methano-3-benzazocine, having the molecular formula $C_{20}H_{29}N$. This compound was treated with hydrochloric acid to convert it to the hydrochloride, a white crystalline solid which weighed 6.0 g. and melted at 246°–249° C. The hydrochloride was soluble in water to the extent of 1.0 percent (cloudy solution). The pH of the 1.0 percent aqueous solution was 6.2, and a precipitate formed when the pH was adjusted to 6.3 by addition of N/10 sodium hydroxide solution.

EXAMPLE 7

1,2,3,4,5,6-Hexahydro-3-(2-cyclopropylethyl)-6-methyl-11-ethyl-2,6-methano-3-benzazocine When cyclopropaneacetyl chloride in equivalent amount is substituted for the cyclopropanecarbonyl chloride reactant and racemic 1,2,3,4,5,6-hexahydro-cis-(6-methyl-11-ethyl)-2,6-methano-3-benzazocine is substituted for the corresponding 6,11-dimethyl starting compound in the N-acylation procedure in Example 1A, the amide product obtained is racemic 1,2,3,4,5,6-hexahydro-3-cyclopropaneacetyl-cis-(6-methyl-11-ethyl)-2,6-methano-3-benzazocine; and reduction of this amide with lithium aluminum hydride in tetrahydrofuran yields racemic 1,2,3,4,5,6-hexahydro-3-(2-cyclopropylethyl)-cis-(6-methyl-11-ethyl)-2,6-methano-3-benzazocine.

EXAMPLE 8

1,2,3,4,5,6-Hexahydro-3-(3-cyclopentylpropyl)-6,11-dimethyl-2,6-methano-3-benzazocine When cyclopentanepropionyl chloride in equivalent amount is substituted for the cyclopropanecarbonyl chloride reactant in the N-acylation procedure in Example 1A, the amide product obtained is racemic 1,2,3,4,5,6-hexahydro-3-(cyclopentanepropionyl)-cis-6,11-dimethyl-2,6-methano-3-benzazocine; and reduction of this amide with lithium aluminum hydride in tetrahydrofuran yields racemic 1,2,3,4,5,6-hexahydro-3-(3-cyclopentylpropyl)-cis-6,11-dimethyl-2,6-methano-3-benzazocine.

EXAMPLE 9

1,2,3,4,5,6-Hexahydro-3-(4-cyclohexylbutyl)-6,11-dimethyl-2,6-methano-3-benzazocine When cyclohexylbutyryl chloride in equivalent amount is substituted for the cyclopropanecarbonyl chloride reactant in the N-acylation procedure in Example 1A, the amide product obtained is racemic 1,2,3,4,5,6-hexahydro-3-(cyclohexanebutyryl)-cis-6,11-dimethyl-2,6-methano-3-benzazocine; and the reduction of this amide with lithium aluminum hydride in tetrahydrofuran yields racemic 1,2,3,4,5,6-hexahydro-3-(4-cyclohexylbutyl)-cis-6,11-dimethyl-2,6-methano-3-benzazocine.

EXAMPLE 10

1,2,3,4,5,6-Hexahydro-(3-methyl-2-butenyl)-6,11-dimethyl-2,6-methano-3-benzazocine A stirred mixture of 12.4 g. of racemic 1,2,3,4,5,6-hexahydro-cis-6,11-dimethyl-2,6-methano-3-benzazocine, 7.7 g. of sodium bicarbonate, 200 ml. of dimethyl formamide and 9.3 g. of 1-bromo-3-methyl-2-butene (dimethyl allyl bromide) was refluxed for 4 hours. The reaction mixture was filtered, the filtrate concentrated, and the residue dissolved in diethyl ether. The ethereal solution was washed with water and then with dilute hydrochloric acid solution. The acidic aqueous solution was made basic with dilute sodium hydroxide solution and extracted with diethyl ether. The ethereal solution was dried and concentrated and the liquid residue distilled under reduced pressure. There was obtained 14.3 g. of racemic 1,2,3,4,5,6-hexahydro-3-(3-methyl-2-butenyl)-cis-6,11-dimethyl-2,6-methano-3-benzazocine distilling at 129° C. at 0.9 mm. This base, having the molecular formula $C_{19}H_{27}N$, was converted to its hydrochloride salt which was crystallized from isopropyl alcohol-diethyl ether mixture using decolorizing charcoal to give white crystals melting at 216°–218° C. The solubility of the hydrochloride in water was to 20 percent. The pH of a one percent solution was 6.1 and when the pH was adjusted to 7.0 by the gradual addition of N/10 sodium hydroxide solution, no precipitate was formed.

EXAMPLE 11

1,2,3,4,5,6-Hexahydro-3-(2-methyl-2-propenyl)-6,11-dimethyl-2,6-methano-3-benzazocine Using a procedure similar to that described in Example 10 hereinabove, when 1-chloro-2-methyl-2-propene is reacted with racemic 1,2,3,4,5,6-hexahydro-cis-6,11-dimethyl-2,6-methano-3-benzazocine there is obtained as the product racemic 1,2,3,4,5,6-hexahydro-3-(2-methyl-2-propenyl)-cis-6,11-dimethyl-2,6-methano-3-benzazocine having the molecular formula $C_{18}H_{25}N$.

EXAMPLE 12

1,2,3,4,5,6-Hexahydro-3-(3-hexenyl)-6,11-dimethyl-2,6-methano-3-benzazocine

Following the procedure described in Example 10 hereinabove but substituting 1-bromo-3-hexene for the 1-bromo-3-methyl-2-butene used in that example, the product obtained is racemic 1,2,3,4,5,6-hexahydro-3-(3-hexenyl)-cis-6,11-dimethyl-2,6-methano-3-benzazocine having the molecular formula $C_{20}H_{29}N$.

EXAMPLE 13

1,2,3,4,5,6-Hexahydro-3-(3-chloro-2-propenyl)-6,11-dimethyl-2,6-methano-3-benzazocine Following the procedure described in Example 10 hereinabove but substituting 1,3-dichloro-1-propene for the 1-bromo-3-methyl-2-butene used in that example, there is obtained racemic 1,2,3,4,5,6-hexahydro-3-(3-chloro-2-propenyl)-6,11-cis-dimethyl-2,6-methano-3-benzazocine having the molecular formula $C_{17}H_{22}ClN$.

EXAMPLE 14

1,2,3,4,5,6-Hexahydro-3-(3-chloro-2-propenyl)-6-methyl-2,6-methano-3-benzazocine Following the procedure described in Example 10 hereinabove but substituting racemic 1,2,3,4,5,6-hexahydro-6-methyl-2,6-methano-3-benzazocine for the corresponding 6,11-dimethyl compound used in that example, there is obtained racemic 1,2,3,4,5,6-hexahydro-3-(3-chloro-2-propenyl)-6-methyl-2,6-methano-3-benzazocine having the molecular formula $C_{16}H_{20}ClN$.

EXAMPLE 15

1,2,3,4,5,6-Hexahydro-3-(3,3-dichloro-2-propenyl)-6,11-dimethyl-2,6-methano-3-benzazocine Following the procedure described in Example 10 hereinabove but using 1,3,3-trichloro-2-propene instead of 1-bromo-3-methyl-2-butene as the alkylating agent, there is obtained 1,2,3,4,5,6-hexahydro-3-(3,3-dichloro- 2-propenyl)-cis-6,11-dimethyl-2,6-methano-3-benzazocine having the molecular formula $C_{17}H_{21}Cl_2N$.

EXAMPLE 16

1,2,3,4,5,6-Hexahydro-3-(2-bromo-3-methyl-2-butenyl)-6,11-dimethyl-2,6-methano-3-benzazocine Following the procedure described in Example 10 hereinabove but substituting 1,2-dibromo-3-methyl-2-butene for the 1-bromo-3-methyl-2-butene used in that example, there is obtained racemic 1,2,3,4,5,6-hexahydro-3-(2-bromo-3-methyl-2-butenyl)-cis-6,11-dimethyl-2,6-methano-3-benzazocine having the molecular formula $C_{19}H_{26}BrN$.

EXAMPLE 17

1,2,3,4,5,6-Hexahydro-3-(2-chloro-2-propenyl)-6,11-dimethyl-2,6-methano-3-benzazocine Using a procedure similar to that described in Example 10 hereinabove but using 1,2-dichloro-2-propene instead of 1-bromo-3-methyl-2-butene there is obtained racemic 1,2,3,4,5,6-hexahydro-3-(2-chloro-2-propenyl)-cis-6,11-dimethyl-2,6-methano-3-benzazocine having the molecular formula $C_{17}H_{22}ClN$.

EXAMPLE 18

1,2,3,4,5,6-Hexahydro-3-(3,3-dichloro-2-propenyl)-6-ethyl-11-methyl-2,6-methano-3-benzazocine Following a procedure similar to that described in Example 10 hereinabove but using 1-bromo-3,3-dichloro-2-propene and racemic 1,2,3,4,5,6-hexahydro-cis-(6-ethyl-11-methyl)-2,6-methano-3-benzazocine as the reactants, there is obtained racemic 1,2,3,4,5,6-hexahydro-3-(3,3-dichloro-2-propenyl)-cis-(6-ethyl-11-methyl)-2,6-methano-3-benzazocine having the molecular formula $C_{18}H_{23}Cl_2N$.

EXAMPLE 19

1,2,3,4,5,6-Hexahydro-3-cyanomethyl-6,11-dimethyl-2,6-methano-3-benzazocine

Following a procedure similar to that described in Example 10 hereinabove but using chloroacetonitrile instead of 1-bromo-3-methyl-2-butene there is obtained as the product racemic 1,2,3,4,5,6-hexahydro-3-cyanomethyl-cis-6,11-dimethyl-2,6-methano-3-benzazocine having the molecular formula $C_{16}H_{20}N_2$.

EXAMPLE 20

1,2,3,4,5,6-Hexahydro-3-(2-cyanoethyl)-6,11-dimethyl-2,6-methano-3-benzazocine

To 10.1 g. of racemic 1,2,3,4,5,6-hexahydro-cis-6,11-dimethyl-2,6-methano-3-benzazocine there was added at room temperature 5.0 ml. of acrylonitrile. The reaction mixture was heated on a steam bath for 4 hours and was then distilled under reduced pressure to yield 9.7 g. of racemic 1,2,3,4,5,6-hexahydro-3-(2-cyanoethyl)-cis-6,11-dimethyl-2,6-methano-3-benzazocine having the molecular formula $C_{17}H_{22}N_2$. The pale yellow liquid distilled at 148°–152° C. at 0.5 mm.

Alternatively, this same product is obtained by using 3-chloropropionitrile instead of 1-bromo-3-methyl-2-butene in the procedure described hereinabove in Example 10.

EXAMPLE 21

1,2,3,4,5,6-Hexahydro-3-(3,3-dicyanoallyl)-6,11-dimethyl-2,6-methano-3-benzazocine Following the procedure described in Example 10 hereinabove but substituting 1-chloro-3,3-dicyano-2-propene for the 1-bromo-3-methyl-2-butene used in that example, there is obtained racemic 1,2,3,4,5,6-hexahydro-3-(3,3-dicyanoallyl)-cis-6,11-dimethyl-2,6-methano-3-benzazocine having the molecular formula $C_{19}H_{21}N_3$.

EXAMPLE 22

1,2,3,4,5,6-Hexahydro-3-allyl-6,11-dimethyl-2,6-methano-3-benzazocine

Following the procedure described in Example 10 hereinabove, but substituting allyl bromide for the 1-bromo-3-methyl-2-butene used in that example, the product obtained was racemic 1,2,3,4,5,6-hexahydro-3-allyl-cis-6,11-dimethyl-2,6-methano-3-benzazocine having the molecular formula $C_{17}H_{23}N$. The hydrochloride of this base was a white powder which melted at 271°–272° C. (dec.)

EXAMPLE 23

1,2,3,4,5,6-Hexahydro-3-(3-cyanoallyl)-6,11-dimethyl-2,6-methano-3-benzazocine

Following the procedure described in Example 10 hereinabove but substituting 3-cyanoallyl bromide for the 1-bromo-3-methyl-2-butene used in that example, there is obtained racemic 1,2,3,4,5,6-hexahydro-3-(3-cyanoallyl)-cis-6,11-dimethyl-2,6-methano-3-benzazocine having the molecular formula $C_{18}H_{22}N_2$.

EXAMPLE 24

1,2,3,4,5,6-Hexahydro-3-(2-carboxyethyl)-6,11-dimethyl-2,6-methano-3-benzazocine A mixture of 4.7 g. of racemic 1,2,3,4,5,6hexahydro-3-(2-cyanoethyl)-cis-6,11-dimethyl-2,6-methano-3-benzazocine, 25.0 ml. of concentrated hydrochloric acid and 25.0 ml. of water, was heated at reflux for 3 hours. The reaction mixture was concentrated under reduced pressure and the white solid residue recrystallized from water using decolorizing charcoal. The product was dried under reduced pressure at 70° C. to yield 3.1 g. of racemic 1,2,3,4,5,6-hexahydro-3-(2-carboxyethyl)-cis-6,11-dimethyl-2,6-methano-3-benzazocine hydrochloride melting at 227°–230° C. and having the molecular formula $C_{17}H_{23}NO_2.HCl$. The hydrochloride was soluble in water to 10 percent, the pH of a one percent solution being 3.0. When the pH of the 1 percent solution was gradually adjusted to 7.0 by the addition of N/10 sodium hydroxide solution, no precipitate formed.

EXAMPLE 25

1,2,3,4,5,6-Hexahydro-3-(2-carbamylethyl)-6,11-dimethyl-2,6-methano-3-benzazocine Using a procedure like that described in Example 20 hereinabove, 24.7 g. of racemic 1,2,3,4,5,6-hexahydro-cis-6,11-dimethyl-2,6-methano-3-benzazocine and 13.0 ml. of acrylonitrile were reacted to yield 23.1 g. of racemic 1,2,3,4,5,6-hexahydro-3-(2-cyanoethyl)-cis-6,11-dimethyl-2,6-methano-3-benzazocine. This product (23.0 g.) was mixed with 65.0 ml. of concentrated hydrochloric acid and the mixture was held at 0° C. for 6 hours. The reaction mixture was poured onto ice and ammonium hydroxide added to the stirred mixture causing an oil to separate. The oil was extracted with diethyl ether and the dried ethereal solution concentrated to yield 22.9 g. of crude racemic 1,2,3,4,5,6-hexahydro-3-(2-carbamylethyl)-cis-6,11-dimethyl-2,6-methano-3-benzazocine, having the molecular formula $C_{17}H_{24}N_2O$.

EXAMPLE 26

1,2,3,4,5,6-Hexahydro-3-(3-aminopropyl)-6,11-dimethyl-2,6-methano-3-benzazocine

Racemic 1,2,3,4,5,6-hexahydro-3-(2-carbamylethyl)-cis-6,11-dimethyl-2,6-methano-3-benzazocine (22.9 g.) was reduced with lithium aluminum hydride (10.0 g.) in tetrahydrofuran under reflux for 7 hours to produce 19.2 g. of a yellow syrup. To this syrup (22.3 g.) there was added, with cooling, 25.0 ml. of acetic anhydride. The mixture was heated on a steam bath for 1 hour and was then concentrated in vacuo. The liquid residue was dissolved in diethyl ether and the ethereal solution was extracted with dilute acetic acid solution. The acetic acid solution was washed with ethyl acetate and to the water solution was added potassium carbonate, thus yielding a red oil. The oil was extracted with diethyl ether and the dried ethereal solution concentrated. The residual syrup was mixed with 25.0 ml. of water and 25.0 ml. of concentrated hydrochloric acid and the mixture refluxed for 9 hours. The reaction mixture was concentrated in vacuo and the liquid residue redissolved in water. The solution was treated with decolorizing charcoal and filtered, and to the filtrate there was added potassium hydroxide causing a red oil to separate. The oil was dissolved in diethyl ether and the dried ethereal solution concentrated. The residual oil was distilled under reduced pressure to yield 7.0 g. of racemic 1,2,3,4,5,6-hexahydro-3-(3-aminopropyl)-cis-6,11-dimethyl-2,6-methano-3-benzazocine having the molecular formula $C_{17}H_{26}N_2$ and distilling at 123°–126° C. at 0.1 mm. This base was converted to its dihydrochloride salt having a melting point of 267°–269° C. and being soluble in water to 20 percent. The pH of a one percent solution was 6.6 and when the pH was adjusted to 7.0 by the gradual addition of N/10 sodium hydroxide solution, no precipitate was formed.

EXAMPLE 27

1,2,3,4,5,6-Hexahydro-3-(2-aminoethyl)-6,11-dimethyl-2,6-methano-3-benzazocine

When racemic 1,2,3,4,5,6-hexahydro-3-carbamylmethyl-cis-6,11-dimethyl-2,6-methano-3-benzazocine is used in the procedure described in Example 26 instead of the corresponding 3-(2-carbamylethyl)compound, the product obtained is racemic 1,2,3,4,5,6-hexahydro-3-(2-aminoethyl)-cis-6,11-dimethyl-2,6-methano-3-benzazocine. The starting 3-carbamylmethyl compound having the molecular formula $C_{16}H_{22}N_2O$ is obtained by hydrolysis of racemic 1,2,3,4,5,6-hexahydro-3-cyanomethyl-cis-6,11-dimethyl-2,6-methano-3-benzazocine by a procedure similar to that described in Example 25 for preparation of the corresponding 3-(2-carbamylethyl)compound.

EXAMPLE 28

1,2,3,4,5,6-Hexahydro-3-(tetrahydro-2-furylmethyl)-6,11-dimethyl-2,6-methano-3-benzazocine To a solution of 5.8 g. of tetrahydro-2-furoic acid and 7.0 ml. of triethylamine in 60 ml. of acetone there was added at −10° C. 7.0 ml. of isobutyl chloroformate. To this stirred mixture there was added 8.0 g. of racemic 1,2,3,4,5,6-hexahydro-cis-6,11-dimethyl-2,6-methano-3-benzazocine dissolved in 80 ml. of chloroform. The reaction mixture was held at room temperature for 24 hours and after filtration was concentrated to yield 11.2 g. of a mixture of diastereo isomers of 1,2,3,4,5,6-hexahydro-3-(tetrahydro-2-furoyl)-cis-6,11-dimethyl-2,6-methano-3-benzazocine. This amide (11.2 g.) was reduced for about 5 hours with lithium aluminum hydride (2.0 g.) to yield 6.5 g. of a mixture of diastereo isomers of 1,2,3,4,5,6-hexahydro-3-(tetrahydro-2-furylmethyl)-cis-6,11-dimethyl-2,6-methano-3-benzazocine, having the molecular formula $C_{19}H_{27}NO$. This base was a pale yellow liquid which distilled at 128° C. at 0.1 mm. Its solubility in water was less than 0.25 percent; and its solubility in 95 percent ethyl alcohol was to 5 percent (w/v); a precipitate formed when this solution was diluted with four volumes of water.

EXAMPLE 29

1,2,3,4,5,6-Hexahydro-3-(tetrahydro-3-furylmethyl)-6,11-dimethyl-2,6-methano-3-benzazocine Following the procedure described hereinabove in Example 28, but using tetrahydro-3-furoic acid instead of tetrahydro-2-furoic acid, there is obtained as the intermediate amide 1,2,3,4,5,6-hexahydro-3-(tetrahydro-3-furoyl)-cis-6,11-dimethyl-2,6-methano-3-benzazocine; and, as the final product, 1,2,3,4,5,6-hexahydro-3-(tetrahydro-3-furylmethyl)-cis-6,11-dimethyl-2,6-methano-3-benzazocine having the molecular formula $C_{19}H_{27}NO$.

EXAMPLE 30

1,2,3,4,5,6-Hexahydro-6,11-dimethyl-3-[2-(3-indolyl)ethyl]-2,6-methano-3-benzazocine Following a procedure similar to that described in Example 28 hereinabove, 17.5 g. of racemic 1,2,3,4,5,6-hexahydro-cis-6,11-dimethyl-2,6-methano-3-benzazocine was interacted with 10.1 g. of 3-indoleacetic acid and 14.0 ml. of isobutyl chloroformate to yield 25.0 g. of a liquid mixture consisting of racemic 1,2,3,4,5,6-hexahydro-3-(3-indoleacetyl)-cis-6,11-dimethyl-2,6-methano-3-benzazocine and by-products. This mixture (25.0 g.) was reduced for 6 hours with lithium aluminum hydride (5.0 g.) to yield 20.0 g. of a liquid residue. The residue was dissolved in diethyl ether and to the ethereal solution there was added 10.7 g. of ethanesulfonic acid causing a red syrup to be precipitated. The ether was decanted and the syrup was washed by decantation with fresh ether. The ether washes were discarded and the red syrup was mixed with a solution of 20 g. of potassium carbonate dissolved in 100 ml. of water. An oil separated and was extracted with diethyl ether, the ethereal solution dried and then concentrated. The residual oil was distilled under reduced pressure and the fraction distilling at 223°–232° C. at 0.1 mm. was fractionated by column chromatography (magnesium silicate-hexane-ether) to yield 3.1 g. of racemic 1,2,3,4,5,6-hexahydro-3-[2-(3-indolyl)ethyl]-cis-6,11-dimethyl-2,6-methano-3-benzazocine having the molecular formula $C_{24}H_{28}N_2$. This base was converted to its monohydrochloride which was recrystallized from isopropyl alcohol. The white crystalline solid melted at 255°–258° C. and its solubility in water was less than 0.25 percent. Its solubility in 95 percent ethyl alcohol was less than one percent (w/v).

EXAMPLE 31

1,2,3,4,5,6-Hexahydro-3-[2-(3-indolyl)ethyl-6,11-dimethyl]-2,6-methano-3-benzazocine Following the procedure described in Example 30 hereinabove, but substituting 2-indoleacetic acid for the 3-indoleacetic acid used in that example, there is obtained as the intermediate amide racemic 1,2,3,4,5,6-hexahydro-3-(2-indoleacetyl)-cis-6,11-dimethyl-2,6-methano-3-benzazocine; and, as the final product, racemic 1,2,3,4,5,6-hexahydro-3-[2-(2-indolyl)ethyl]-cis-6,11-dimethyl-2,6-methano-3-benzazocine having the molecular formula $C_{24}H_{28}N_2$.

EXAMPLE 32

1,2,3,4,5,6-Hexahydro-3-(n-butylcarbamyl)-6,11-dimethyl-2,6-methano-3-benzazocine To a solution of 2.2 g. of n-butyl isocyanate in 10 ml. of chloroform there was added a solution of 4.3 g. of racemic 1,2,3,4,5,6-hexahydro-cis-6,11-dimethyl-2,6-methano-3-benzazocine in 10 ml. of chloroform. An exothermic reaction resulted and when the reaction temperature had returned to 25° C. after about 25 minutes, the reaction was concentrated under reduced pressure. The residual yellow oil was distilled under reduced pressure to give 4.7 g. of a liquid product distilling at 135°–191° C. at 0.1 mm. This product was then fractionated by column chromatography (silica-chloroform-methyl alcohol) to give 2.7 g. of racemic 1,2,3,4,5,6-hexahydro-3-(n-butylcarbamyl)-cis-6,11-dimethyl-2,6-methano-3-benzazocine having the molecular formula $C_{19}H_{28}N_2O$. The clear viscous liquid was soluble in water to 20 percent. A one percent solution had a pH of 9.2 and when the pH was adjusted to 7.0 by the gradual addition of N/10 hydrochloric acid solution, no precipitate was formed.

EXAMPLE 33

1,2,3,4,5,6-Hexahydro-3-(sec-butylcarbamyl)-6,11-dimethyl-2,6-methano-3-benzazocine By substituting sec-butyl isocyanate for n-butyl isocyanate in the procedure described in Example 35 hereinabove, there is obtained as the product racemic 1,2,3,4,5,6-hexahydro-3-(sec-butylcarbamyl)-cis-6,11-dimethyl-2,6-methano-3-benzazocine.

EXAMPLE 34

1,2,3,4,5,6-Hexahydro-3-nicotinoyl-6,11-dimethyl-2,6-methano-3-benzazocine

To a stirred mixture of 2.7 g. of nicotinic acid, 3.1 ml. of triethylamine and 30.0 ml. of acetone there was added at 0° C. 3.1 ml. of isobutyl chloroformate. After ten minutes a solution of 4.4 g. of racemic 1,2,3,4,5,6-hexahydro-cis-6,11-dimethyl-2,6-methano-3-benzazocine in 50.0 ml. of acetone was added to the reaction mixture at 0° C. The internal temperature was permitted to rise to 25° C. and stirring was continued for 4 hours. The reaction mixture was filtered and the filtrate was concentrated under reduced pressure. The residue was dissolved in ethyl acetate and the solution washed with water and dilute sodium bicarbonate solution. The dried ethyl acetate solution was concentrated under reduced pressure to yield 6.0 g. of racemic 1,2,3,4,5,6-hexahydro-3-nicotinoyl-cis-6,11-dimethyl-2,6-methano-3-benzazocine having the molecular formula $C_{20}H_{22}N_2O$. This base was converted to its hydrochloride salt by treatment with a diethyl ether solution of anhydrous hydrogen chloride. The hydrochloride salt recrystallized from ethyl acetateisopropyl alcohol, melted at 201°–208° C. and was soluble in water to 20 percent. The pH of a one percent solution was 2.7 and when a N/10 sodium hydroxide solution was added gradually, a precipitate formed at pH 3.0.

EXAMPLE 35

1,2,3,4,5,6-Hexahydro-3-isonicotinoyl-6,11-dimethyl-2,6-methano-3-benzazocine

Following the procedure described in Example 34 hereinabove, but substituting isonicotinic acid for nicotinic acid, there is obtained racemic 1,2,3,4,5,6-hexahydro-3-isonicotinoyl-cis-6,11-dimethyl-2,6-methano-3-benzazocine having the molecular formula $C_{20}H_{22}N_2O$.

EXAMPLE 36

1,2,3,4,5,6-Hexahydro-3-picolinoyl-6,11-dimethyl-2,6-methano-3-benzazocine

Following the procedure described in Example 27 hereinabove, but substituting picolinic acid for nicotinic acid, there is obtained racemic 1,2,3,4,5,6-hexahydro-3-picolinoyl-cis-6,11-dimethyl-2,6-methano-3-benzazocine having the molecular formula $C_{20}H_{22}N_2O$.

EXAMPLE 37

1,2,3,4,5,6-Hexahydro-3-(1-methylimidazol-5-yl)methyl-6,11-dimethyl-2,6-methano-3-benzazocine A stirred mixture of 7.8 g. of racemic 1,2,3,4,5,6-hexahydro-cis-6,11-dimethyl-2,6-methano-3-benzazocine, 6.6 g. of sodium bicarbonate, 6.3 g. of 1-methyl-5-(chloromethyl)imidazole hydrochloride, and 40 ml. of N,N-dimethylformamide was refluxed for 3½ hours. The reaction mixture was filtered and the filtrate concentrated to yield a syrup-solid mixture which was triturated with ethyl acetate and filtered. The ethyl acetate filtrate was concentrated to yield a solid which was recrystallized from ethyl acetate using decolorizing charcoal. There was thus obtained 2.7 g. of racemic 1,2,3,4,5,6-hexahydro-3-(1-methylimidazol-5-yl)methyl-cis-6,11-dimethyl-2,6-methano-3-benzazocine melting at 160°–161° C. and having a molecular formula of $C_{19}H_{25}N_3$. Its solubility in water was less than 0.25 percent whereas in 95 percent ethyl alcohol it was soluble to 5 percent (w/v) from which solution the product was precipitated by the gradual addition of four volumes of water.

EXAMPLE 38

1,2,3,4,5,6-Hexahydro-6,11-dimethyl-3-(1-n-butylimidazol-5-yl)methyl-2,6-methano-3-benzazocine By replacing 1-methyl-5-chloromethylimidazole hydrochloride with 1-n-butyl-5-(chloromethyl)imidazole hydrochloride in the procedure described in Example 37 hereinabove, the product obtained is racemic 1,2,3,4,5,6-hexahydro-3-(1-n-butylimidazol-5-yl)methyl-cis-6,11-dimethyl-2,6-methano-3-benzazocine having the molecular formula $C_{22}H_{31}N_3$.

EXAMPLE 39

1,2,3,4,5,6-Hexahydro-3-(2,2-dimethoxyethyl)-6,11-dimethyl-2,6-methano-3-benzazocine A stirred mixture of 6.7 g. of racemic 1,2,3,4,5,6-hexahydro-cis-6,11-dimethyl-2,6-methano-3-benzazocine, 5.0 g. of sodium bicarbonate, 6.2 g. of bromoacetaldehyde dimethyl acetal, and 65.0 ml. of N,N-dimethylformamide was refluxed for 2½ hours and then held at 25° C. for 12 hours. The reaction mixture was filtered and the filtrate was concentrated under reduced pressure. The residue was mixed with water and extracted with diethyl ether. The dried ethereal solution was concentrated and the residual syrup was distilled under reduced pressure. There was thus obtained 6.7 g. of racemic 1,2,3,4,5,6-hexahydro-3-(2,2-dimethoxyethyl)cis-6,11-dimethyl-2,6-methano-3-benzazocine as a yellow liquid distilling at 147°–149° C. at 1.8 mm. and having the molecular structure $C_{18}H_{27}NO_2$. This base was treated with a diethyl ether solution of anhydrous hydrogen chloride to yield its hydrochloride salt melting at 187°–188° C. The salt was soluble in water to 20 percent. The pH of a 1 percent solution was 5.9 and when the pH was adjusted to 7.0 by the gradual addition of N/10 sodium hydroxide solution, no precipitate formed.

EXAMPLE 40

1,2,3,4,5,6-Hexahydro-3-cyclopropylmethyl-6,11-diethyl-2,6-methano-3-benzazocine A mixture of 2.65 g. of racemic 1,2,3,4,5,6-hexahydro-cis-6,11-diethyl-2,6-methano-3-benzazocine hydrochloride, 1.60 g. of cyclopropylmethyl bromide, 2.0 g. of sodium bicarbonate and 25 ml. of dimethylformamide was stirred under reflux, then filtered. The filter cake was washed with ethanol and the filtrate was concentrated. Water and ether were added to the residue and the ether layer was washed with water, dried and charcoaled. Hydrogen chloride was added to the resulting ether solution of racemic 1,2,3,4,5,6-hexahydro-3-cyclopropylmethyl-cis-6,11-diethyl-2,6-methano-3-benzazocine having the molecular formula $C_{20}H_{29}N$. Recrystallization of the resulting white solid (2.76 g., m.r. 159°–179° C.) from ethyl acetate gave the hydrochloride salt, which melted at 181°–183° C.

The following are further illustrative examples of the compounds of this invention which are obtained by proceeding in accordance with the methods hereinabove described:

1,2,3,4,5,6-hexahydro-3-(cyclohexylmethyl)-6,11-dimethyl-2,6-methano-3-benzazocine;

1,2,3,4,5,6-hexahydro-3-(2-cyclohexylpropyl)-6,11-dimethyl-2,6-methano-3-benzazocine;

1,2,3,4,5,6-hexahydro-3-cyclopropylmethyl-6-(n-propyl)-11-methyl-2,6-methano-3-benzazocine;

1,2,3,4,5,6-hexahydro-3-(4-cyclopropylbutyl)-6,11-dimethyl-2,6-methano-3-benzazocine;

1,2,3,4,5,6-hexahydro-3-cyclopropylmethyl-6-(n-butyl)-11-methyl-2,6-methano-3-benzazocine;

1,2,3,4,5,6-hexahydro-3-cyclopropylmethyl-6-methyl-2,6-methano-3-benzazocine; and 1,2,3,4,5,6-hexahydro-3-(3-cyclopropylpropyl)-6,11-dimethyl-2,6-methano-3-benzazocine.

The compounds of this invention having in free base form Formula I hereinabove have useful central depressant and psychomotor action when administered subcutaneously, intraperitoneally or perorally, and are formulated for such use by conventional means into the conventional dosage forms employed in the pharmaceutical art. Some species of Formula I produce stimulation at low dosages and depression at higher doses.

The compound of Example 37 was active at a dose of 100 mg./kg. subcutaneously as a skeletal muscle relaxant with side-effect CNS stimulation in the inclined screen test in mice, wherein a group of 10 mice at the test dose were placed on an inclined wire screen immediately after dosing, those mice developing typical skeletal muscle relaxation and sliding off the screen within 30 or 60 minutes after injection were considered positive reactors and a test compound was considered active if one or more mice fell off the screen.

The preferred species of this invention, i.e. the compounds having in free base form Formula II, are useful as analgesic agents administered orally or parenterally to humans. Moreover, these preferred compounds were found to be active in one or both of two different standard anti-convulsant screening tests in mice, namely in anti-maximal electroshock seizures and in anti-maximal pentylenetetrazol seizures. In the anti-maximal electroshock seizure test, the compounds were administered intraperitoneally or perorally 30 or 90 minutes prior to the application of 50 milliamperes of alternating current through corneal electrodes. Shock duration was 0.3 second. The criterion for anticonvulsant activity was the absence of the tonic hind leg extensor component of the seizure. In the anti-maximal pentylenetetrazol seizure test, the compounds were given intraperitoneally 30 or 90 minutes prior to the rapid intravenous injection of 50 mg. per kg. of pentylenetetrazol. Failure to display tonic hind leg extensor seizures was again the criterion for drug action. Representative results, expressed as $ED_{50}$ (mg./kg.), which were obtained with my new compounds in these two tests are as follows:

| Cpd. of Ex. No. | Anti-Maximal Electroshock | | | | Anti-Maximal Pentylenetetrazol | | | |
|---|---|---|---|---|---|---|---|---|
| | PO | | IP | | PO | | IP | |
| | 30' | 90' | 30' | 90' | 30' | 90' | 30' | 90' |
| 1A | 26.2 ± 7 | 35.5 ± 3 | 11.2 ± 2 | INACT. | 3.3 ± .8 | 6.2 ± 1 | 2.3 ± 7 | 5.3 ± 10 |
| 4 | inact. | | 30.5 ± 5.8 | INACT. | INACT. | 25.8 ± 7 | 13.2 ± 3 | 26.2 ± 8.1 |
| 6 | INACTIVE | | | | INACTIVE | | 11.7 ± 2 | 8 ± 3 |

These compounds were inactive when tested for analgesic activity in rats in a modified D'Amour-Smith test procedure, and they did not potentiate subhypnotic doses of hexobarbital in mice.

1,2,3,4,5,6-Hexahydro-3-cyclopropylmethyl-6,11-dimethyl-2,6-methano-3-benzazocine is a particularly preferred species of the instant invention. The results of representative further biological tests using the racemic cis form of this compound, the product of Example 1A, were as follows:

In anticonvulsant studies, against minimal pentylenetetrazol seizures, wherein the dose of pentylenetetrazol was only 32.5 mg./kg. (intravenously) and the ensuing convulsions were clonic, without a tonic hind leg extensor component, the oral $ED_{50}$ values were: 30 minutes post-medication, 15 ± 4 mg./kg.; 90 minutes post-medication, 37 ± 6 mg./kg.

In psychomotor activity studies in mice, in the range of 8–128 mg./kg. p.o., the compound produced a pattern of stimulation at lower doses and depression at high doses. Ataxia, loss of righting reflex, and death occurred at a dose of 128 mg./kg.

The compound induced significant diuresis in mice at dose levels of 12.5 mg./kg. and 25 mg./kg. i.p., with production of dilute urine without electrolyte concentration. Sixty minutes after oral medication, 50 percent of the mice tested had fallen from a 60° inclined screen at a dose of 38.2 ± 11 mg./kg. The $ED_{50}$ for intraperitoneal administration was 17.2 mg./kg.

In a toxicology study, monkeys were medicated orally with 5 mg./kg. and 25 mg./kg. of the product of Example 1A each day for 5 days. The lower dose was well tolerated. Some ataxia with a decrease in activity was observed. At 25 mg./kg. there was a more marked decrease in spontaneous activity along with ataxia and salivation. There was considerable variability among the monkeys in the magnitude of the response. Symptoms lasted 2 to 5 hours. Some weight loss occurred. Blood SGO-T, alkaline phosphatase, and BUN were all normal. Acute toxicity tests gave the following results:

| Route | $LD_{50}$ ± s.e. mg./kg. | Species | Time |
|---|---|---|---|
| I.V. | 20 ± 1 | mouse | 24 hr. |
| I.V. | 20 ± 1 | mouse | 7 day |
| P.O. | 155 ± 17 | mouse | 24 hr. |
| P.O. | 155 ± 17 | mouse | 7 day |
| I.P. | 65 ± 7 | mouse | 24 hr. |
| I.P. | 65 ± 7 | mouse | 7 day |
| I.V. | 17 ± 1 | rat | 24 hr. |
| I.V. | 17 ± 1 | rat | 7 day |
| P.O. | $ALD_{50}$200 | rat | 24 hr. |
| P.O. | $ALD_{50}$200 | rat | 7 day |

1,2,3,4,5,6-hexahydro-3-cyclopropylmethyl-6,11-dimethyl-2,6-methano-3-benzazocine has been found to be especially useful as a strong analgesic in humans. For example, administered orally, the effective dosage of the racemic cis form of this compound in humans has been determined to be about 0.1 to 0.5 mg. of drug per kg. of body weight per day, at 5–25 mg. per dose; preferably about 0.2 to 0.4 mg./kg./day, for instance a total of 80 mg./day at 20 mg./dose. At effective therapeutic analgesic doses in humans, 1,2,3,4,5,6-hexahydro-3-cyclopropylmethyl-6,11-dimethyl-2,6-methano-3-benzazocine desirably produces only minimal central nervous system effects and, in particular, produces very few, if any, psychotomimetic effects, in contrast with 1,2,3,4,5,6-hexahydro-3-cyclopropylmethyl-8-hydroxy-6,11-dimethyl-2,6-methano-3-benzazocine, a potent analgesic which produces a significant incidence of psychotomimetic effects in humans at analgesically effective doses.

Intermediates

Certain of the intermediate amides afforded by the above described methods are a further aspect of the instant invention. These amides have the structural formula

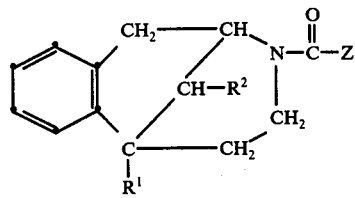

Formula III wherein Z is cycloalkyl, lower alkylcycloalkyl, cycloalkyllower alkyl, lower alkylcycloalkyl-lower alkyl, tetrahydrofuryl, or 2-or 3-indolylmethyl, and $R^1$, $R^2$, cycloalkyl, and lower alkyl have the same significance indicated hereinabove in connection with Formula I.

Starting Materials

The 1,2,3,4,5,6-hexahydro-6-($R^1$)-11-($R^2$)-2,6-methano-3-benzazocine starting materials for the preparation of the compounds of Formula I can be obtained by application of generally known procedures. Thus, 3-($R^2$)-4-($R^1$)-pyridine methiodide is interacted with benzylmagnesium chloride; the resulting N-methyl-2-(benzyl)-3-($R^2$)-4-($R^1$)-1,2-dihydropyridine is reduced with sodium borohydride or by catalytic hydrogenation to produce N-methyl-2-(benzyl)-3-($R^2$)-4-($R^1$)-1,2,5,6-tetrahydropyridine; and this latter product is heated with an appropriate cyclizing agent, such as concentrated hydrobromic or phosphoric acid, to yield a mixture of the racemic cis (also termed the α or "normal" series) and the racemic trans (also termed the β or "iso" series) forms of 1,2,3,4,5,6-hexahydro-3-methyl-6-($R^1$)-11-($R^2$)-2,6-methano-3-benzazocine. The 3-methyl group is removed by treatment with cyanogen bromide to produce the corresponding 3-cyano compound which is converted by heating with dilute hydrochloric acid to the cis and trans forms of 1,2,3,4,5,6-hexahydro-6-($R^1$)-11-($R^2$)-2,6-methano-3-benzazocine. The cis and trans forms of these compounds are readily separated, if desired, by use of conventional techniques, for instance by fractional crystallization or by column chromatography; and, if desired, the racemic mixtures can be resolved by conventional methods into their optically active components. The benzazocine compounds thus obtained as well as the pyridines, dihydropyridines, and tetrahydropyridines intermediate thereto are all old classes of compounds.

The following procedure illustrates the preparation of the starting material racemic 1,2,3,4,5,6-hexahydro-3-methyl-cis-(6-methyl-11-ethyl)-2,6-methano-3-benzazocine:

To a stirred solution of 38.0 g. of 1,4-dimethyl-3-ethylpyridinium iodide in 300 ml. of diethyl ether there was added at room temperature the solution of benzylmagnesium chloride obtained by reacting 3.6 g. of magnesium with 19.0 g. of benzyl chloride in 275 ml. of diethyl ether. The reaction mixture was stirred for one hour and was then poured into a mixture of ice and water containing 50.0 g. of ammonium chloride. The mixture was stirred and sufficient concentrated ammonium hydroxide was added to render the mixture basic to litmus. The ether layer was separated and was extracted twice with 35.0 ml. portions of 1.5N hydrochloric acid solution. The ether layer was discarded and to the aqueous phase there was added with stirring 50.0 ml. of cold concentrated ammonium hydroxide. A yellow oil separated and was extracted with diethyl ether. The ether solution was dried and then concentrated to give a liquid residue weighing 19.0 g. The residue was distilled under reduced pressure to yield 15.2 g. of 2-benzyl-1,4-dimethyl-3-ethyl-1,2-dihydropyridine distilling at 105°–110° C. at 1.2 mm.

A solution of total volume of 200.0 ml. prepared by dissolving 16.7 g. of 2-benzyl-1,4-dimethyl-3-ethyl-1,2-dihydropyridine in 1N hydrochloric acid solution was catalytically hydrogenated at three atmospheres of pressure of hydrogen using 6.0 g. of 5 percent palladium-on-barium sulfate hydrogenation catalyst. Reduction was complete at the end of 4 hours. The solution was filtered and the light yellow filtrate was extracted with benzene to remove a trace of an insoluble oil. The aqueous layer was then treated with concentrated ammonium hydroxide solution and extracted with diethyl ether. The dried ether solution was concentrated and the concentrate distilled under reduced pressure to yield 13.3 g. of 2-benzyl-1,4-dimethyl-3-ethyl-1,2,5,6-tetrahydropyridine distilling at 99°–101° C. at 1.0 mm.

A mixture of 13.3 g. of 2-benzyl-1,4-dimethyl-3-ethyl-1,2,5,6-tetrahydropyridine and 80.0 ml. of 85 percent phosphoric acid was heated at reflux for 61 hours. The reaction mixture was poured into ice containing an excess of concentrated ammonium hydroxide solution. A solid and a yellow oil separated. The mixture was extracted with diethyl ether and the dried ether solution concentrated to give 12.0 g. of an oil. The crude racemic 1,2,3,4,5,6-hexahydro-3-methyl-cis-(6-methyl-11-ethyl)-2,6-methano-3-benzazocine was distilled under reduced pressure to give 11.0 g. of a yellow oil distilling at 101°–102° C. at 0.9 mm. The oil thus obtained was fractionated by column chromatography (alumina-hexane-ether) to give racemic 1,2,3,4,5,6-hexahydro-3-methyl-cis-(6-methyl-11-ethyl)-2,6-methano-3-benzazocine having the molecular formula $C_{16}H_{23}N$. The base was converted to the hydrochloride which after recrystallization from acetone gave 0.85 g. of white crystals which melted at 276.2°–279.0° C. The hydrochloride was soluble in water to 5 percent and the pH of a 1 percent solution was 6.7. When the pH of the 1 percent solution was gradually adjusted to 7.0 by the addition of N/10 sodium hydroxide solution, no precipitate formed. Instead of 3-($R^2$)-4-($R^1$)-pyridine methoiodide the starting material can be 1-benzyl-3-($R^2$)-4-($R^1$)-pyridinium chloride and the N-benzyl can be removed by catalytic hydrogenation after the cyclization step. The following preparation of racemic 1,2,3,4,5,6-hexahydro-cis-6,11-diethyl-2,6-methano-3-benzazocine hydrochloride, the intermediate of Example 40, illustrates this method:

Benzyl chloride (250 g.) was added dropwise to a stirred and refluxed solution of 3,4-diethylpyridine (262 g.) and isopropyl alcohol (700 ml.). Repeated concentration under vacuum and addition of benzene afforded a slurry of crystalline 1-benzyl-3,4-diethyl-pyridinium chloride.

The Grignard reagent prepared from magnesium (85.5 g.), benzyl chloride (407 g.) and ether (3020 ml.) was added to the slurry of 1-benzyl-3,4-diethyl-pyridinium chloride in benzene (2250 ml.). After refluxing the mixture was quenched in ice and ammonium chloride (453 g.). Ammonium hydroxide was added to the mixture. The ether layer was washed with water and concentrated. A solution of sodium borohydride (52 g.) in water (260 ml.) was added to a solution of the residue (712 g.) in ethanol (2 l.). The mixture was stirred, allowed to stand overnight and filtered. The filtrate was concentrated under vacuum. Water and ether were added to the residue. The ether layer was washed with water, dried and concentrated. The residue was distilled under vacuum. The main fractions darkened on exposure to air. Therefore, the sodium borohydride reduction was repeated excluding water. Sodium borohydride (42 g.) was added portionwise with stirring to a solution of the combined main fractions (517 g.) in ethanol (100%, 1 l.). The mixture was stirred for 6 hours, allowed to stand overnight and concentrated. Water and ether were added. The ether layer was washed with water, dried and concentrated. Since the reduction still appeared incomplete, it was repeated using dimethylformamide as the solvent. Sodium borohydride (40 g.) was added portionwise to a solution of the residue in dimethylformamide (1 l.). The mixture was stirred and allowed to stand overnight. Water was added and the mixture was extracted with ether. The ether extracts were washed with water, dried and concentrated. The residue was distilled under vacuum, affording 1,2-dibenzyl-3,4-diethyl-1,2,5,6-tetrahydropyridine (172 g., b.r. 154°–178° C./0.1 mm., mostly at 174° C.).

A mixture of 1,2-dibenzyl-3,4-diethyl-1,2,5,6-tetrahydropyridine (172 g.), hydrobromic acid (48%, 1350 ml.) and acetic acid (50 ml.) was stirred under reflux for a day, then concentrated. Sodium hydroxide (35%) and benzene were added to the residue with heating and agitation. The benzene layer was washed with water, dried and concentrated. The residue was distilled under vacuum, affording 1,2,3,4,5,6-hexahydro-3-benzyl-cis-6,11-diethyl-2,6-methano-3-benzazocine. The fraction boiling at 140° C./0.3 mm.–164° C./0.05 mm. was converted into the oxalate salt, which melted at 210°–212.5° C.

A mixture of 1,2,3,4,5,6-hexahydro-3-benzyl-cis-6,11-diethyl-2,6-methano-3-benzazocine oxalate (8.9 g.), palladium-on-carbon (10%, 0.4 g.) and ethanol (to make the total volume 100 ml.) was hydrogenated in a Parr apparatus at 50° C., then filtered. The filtrate was concentrated and the residue was triturated with ether. Recrystallization of part of the resulting white solid (6.0 g., m.r. 204°–211° C.), first from isopropyl alcohol-ether and then from isopropyl alcohol, afforded 1,2,3,4,5,6-hexahydro-cis-6,11-diethyl-2,6-methano-3-benzazocine hydrochloride, which melted at 208.5°–211° C.

I claim:
1. 1,2,3,4,5,6-Hexahydro-3-(Y)-6-($R^1$)-11-($R^2$)-2,6-methano-3-benzazocine wherein Y is (1-lower alkylimidazol-5-yl)methyl, $R^1$ is lower alkyl and $R^2$ is hydrogen or lower alkyl.
2. A compound according to claim 1 wherein each of $R^1$ and $R^2$ is lower alkyl.
3. A compound according to claim 2 wherein each of $R^1$ and $R^2$ is methyl.
4. A compound according to claim 3 wherein Y is (1-methylimidazolyl-5-yl)methyl.

* * * * *